US006478784B1

(12) United States Patent
Johnson et al.

(10) Patent No.: US 6,478,784 B1
(45) Date of Patent: Nov. 12, 2002

(54) GARMENT HAVING INTEGRALLY-FORMED SURFACE PROTRUSIONS

(75) Inventors: Larry K. Johnson, Milford, OH (US); Mark J. Kline, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 141 days.

(21) Appl. No.: 09/596,219

(22) Filed: Jun. 19, 2000

(51) Int. Cl.[7] .............................................. A61F 13/15
(52) U.S. Cl. .................... 604/385.01; 604/391; 24/442
(58) Field of Search ........................... 604/385.01, 391; 24/442–462

(56) References Cited

U.S. PATENT DOCUMENTS

| | | | |
|---|---|---|---|
| 2,499,898 A | 3/1950 | Anderson | 24/206 |
| 3,081,772 A | 3/1963 | Brooks et al. | 128/287 |
| 4,794,028 A | 12/1988 | Fischer | 428/100 |
| 5,269,776 A | 12/1993 | Lancaster et al. | 604/387 |
| 5,342,344 A | 8/1994 | Lancaster et al. | 604/387 |
| 5,692,271 A | 12/1997 | Provost et al. | 24/452 |
| 5,720,740 A | 2/1998 | Thomas | 604/391 |
| 5,845,375 A | 12/1998 | Miller et al. | 24/452 |
| 5,879,604 A | 3/1999 | Melbye et al. | 264/167 |
| 5,884,374 A | 3/1999 | Clune | 24/446 |
| 5,887,320 A * | 3/1999 | Provost | 24/452 |
| 5,942,177 A * | 8/1999 | Banfield | 264/134 |

FOREIGN PATENT DOCUMENTS

| | | | |
|---|---|---|---|
| EP | 0 418 954 A2 | 3/1991 | A61F/13/58 |
| WO | WO 98/16178 | 4/1998 | A61F/13/15 |

* cited by examiner

*Primary Examiner*—Jeanette Chapman
(74) *Attorney, Agent, or Firm*—Michael S. Kolodesh; Jay A. Krebs; Ken K. Patel

(57) ABSTRACT

A garment or undergarment, such as an absorbent article, having a first region, a second region opposed to the first region and a garment material extending through at least a portion of the first region. The garment material has a surface wherein at least a portion of the surface has been mechanically modified to form a plurality of surface protrusions integrally from the garment material. The garment further includes a landing zone having a plurality of fibrous loops located at least partially in the second waist region and adapted to engage with the surface protrusions of the first region to provide a closure mechanism for holding the first region and the second region in an overlapping configuration. In addition, the integrally-formed surface protrusions can be provided on the inner surface of the garment contacting the skin of the wearer to provide a frictional force between the surface protrusions and the skin of the wearer to provide the garment with desired functional characteristics when in use by the wearer.

23 Claims, 13 Drawing Sheets

Fig. 3A
Fig. 3B
Fig. 3C
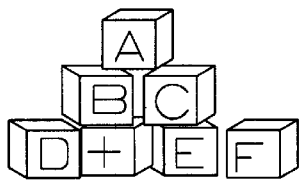
Fig. 3D
Fig. 3E
Fig. 3F
Fig. 3G
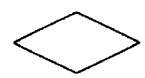
Fig. 3H
Fig. 3I
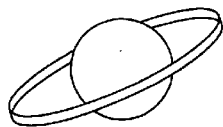
Fig. 3J
Fig. 3K
Fig. 3L
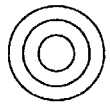
Fig. 3M

GARMENT HAVING INTEGRALLY-FORMED SURFACE PROTRUSIONS

FIELD OF THE INVENTION

The present invention relates to garments having protrusions on a surface of the garment. More particularly, the present invention relates to garments and undergarments, including absorbent articles, such as disposable diapers and feminine protective devices, which have surface protrusions for securing the garment around a wearer. The present invention also relates to articles to be attached to a wearer, such as body wraps having surface protrusions for securing the body wrap around the wearer.

BACKGROUND OF THE INVENTION

Fastening systems for connecting or holding together portions of garment materials are available in many different forms, including buttons, snap fasteners, tape tab fasteners, hook-and-loop fasteners, and the like. Such fastening systems can be utilized on garments and disposable garments, such as absorbent articles, body wraps, bibs, bedsheets, tablecloths and the like.

In the field of absorbent articles, such as disposable diapers and feminine protection devices, various types of fasteners are commonly provided to hold cooperating portions of the structure in a desired spatial relationship. In disposable diapers, for example, a frequently-utilized form of fastener system includes a separately-attached fastener member in the form of a tape tab. Such fastening system includes a first adhesive carried on a portion of the area of one surface of the tab to enable the tab to be securely and non-removably attached to a surface of the garment. A portion of the area of the same tab surface includes a free end that extends from the garment and that carries a second, pressure-sensitive adhesive. A peelable release strip is usually provided to cover and protect the pressure-sensitive adhesive surface until it is to be adhered to another surface. When it is intended to be employed, the release strip is removed from the tape tab to permit the pressure-sensitive adhesive surface to be pressed against and to releasably adhere to a cooperating surface to engage the fastening system. The cooperating surface sometimes carries a separately-applied contact member, generally in the form of a separate strip of material that defines a landing zone that is especially adapted to receive and to releasably retain the pressure-sensitive-adhesive-carrying surface of the tape tab. Examples of such tape tabs and landing zones are described in U.S. Pat. No. 5,151,092, entitled "Absorbent Article With Dynamic Waist Feature Having A Predisposed Resilient Flexural Hinge," which was issued on Sep. 29, 1992, to Buell et al.

Another form of fastening system that has been utilized on garments, including disposable garments such as disposable diapers, is a hook-and-loop type fastening system, one example of which is the trademarked name VELCRO®. When provided in that form, a separately-formed tab member that includes a surface area having a large number of relatively small, outwardly-extending hook elements is generally firmly and securely attached to a portion of the garment, as by an adhesive, by heat sealing, or the like, to provide a hook member. The hook elements are adapted to engage with a second separately-formed, cooperating surface that is securely attached to the garment, as by an adhesive, by heat sealing, or the like, and that carries a plurality of relatively small, outwardly-extending loop elements providing a loop member. The hook member of the fastener system is brought into contact with the loop member and the two fastener members are pressed together to cause the hook elements to engage with and to be retained by the loop elements, to thereby hold together the two portions of the garment that carry the respective hook and loop members. One form of such hook and loop fastener members for a diaper is described in U.S. Pat. No. 3,081,772, entitled "Diaper," which was issued on Mar. 19, 1963, to Brooks et al.

A still further form of fastening system for a disposable diaper, one in which each of the cooperating fastener members is integrally formed as a part of the garment is disclosed in U.S. Pat. No. 5,269,776, entitled "Disposable Diaper With Refastenable Mechanical Fastening System," which issued on Dec. 14, 1993, to Lancaster et al. The fastening system disclosed in that patent includes resiliently interlocking gripping means and target means that are each separately and integrally formed on respective spaced front and rear waist extensions of a disposable diaper. Each of the gripping means and the target means includes a plurality of respective outwardly-extending, interengageable connectors in the form of projections on the gripping means, and correspondingly-configured projection receptacles on the target means. The connectors and receptacles are each oriented to extend perpendicularly relative to the respective surfaces on which they are formed, and they are adapted to be pressed into engaging relationship with each other to retain the associated structural elements together in contacting relationship.

However, the garments having fastening systems described above do not provide enough flexibility and softness in the fastening area itself, sometimes causing physical discomfort to the wearer. Further, the fasteners described above are expensive because both fastener surfaces, i.e., gripping means and target means, need to be formed. Still further, the conventional fastening systems are not complimented with integrally-formed high friction areas intended to contact the skin of the wearer to reduce the tendency of the garment to slip during use.

Therefore, it would be desirable to provide a garment having a fastening system that is more flexible, softer and comfortable to the wearer. Further, it would be desirable to provide a garment having a fastening surface, which is formed integrally from a first region of the garment and is adapted to be releasably engaged with loops in a second region of the garment. Still further, it would be desirable to provide a garment having high friction areas to resist relative movements of the garment in relation to the skin of the wearer in order to provide the garment with the desired functional characteristics when in use by the wearer.

SUMMARY OF THE INVENTION

In accordance with one aspect of the present invention, a garment is provided including a first region and a second region opposed to the first region and a garment material extending through at least a portion of the first region garment material. The garment material has a surface wherein at least a portion of the surface has been mechanically modified to form a plurality of surface protrusions integrally from the garment material and not separately joined to the garment material. The garment further includes a landing zone having a plurality of fibrous loops located at least partially in the second region and adapted to engage with the surface protrusions of the first region to provide a closure mechanism for holding the first region and the second region in an overlapping configuration.

BRIEF DESCRIPTION OF THE DRAWINGS

FIGS. 3A through 3M show examples of surface protrusions area configurations to provide an aesthetically pleasing garment.

DETAILED DESCRIPTION OF THE INVENTION

Figure 1:
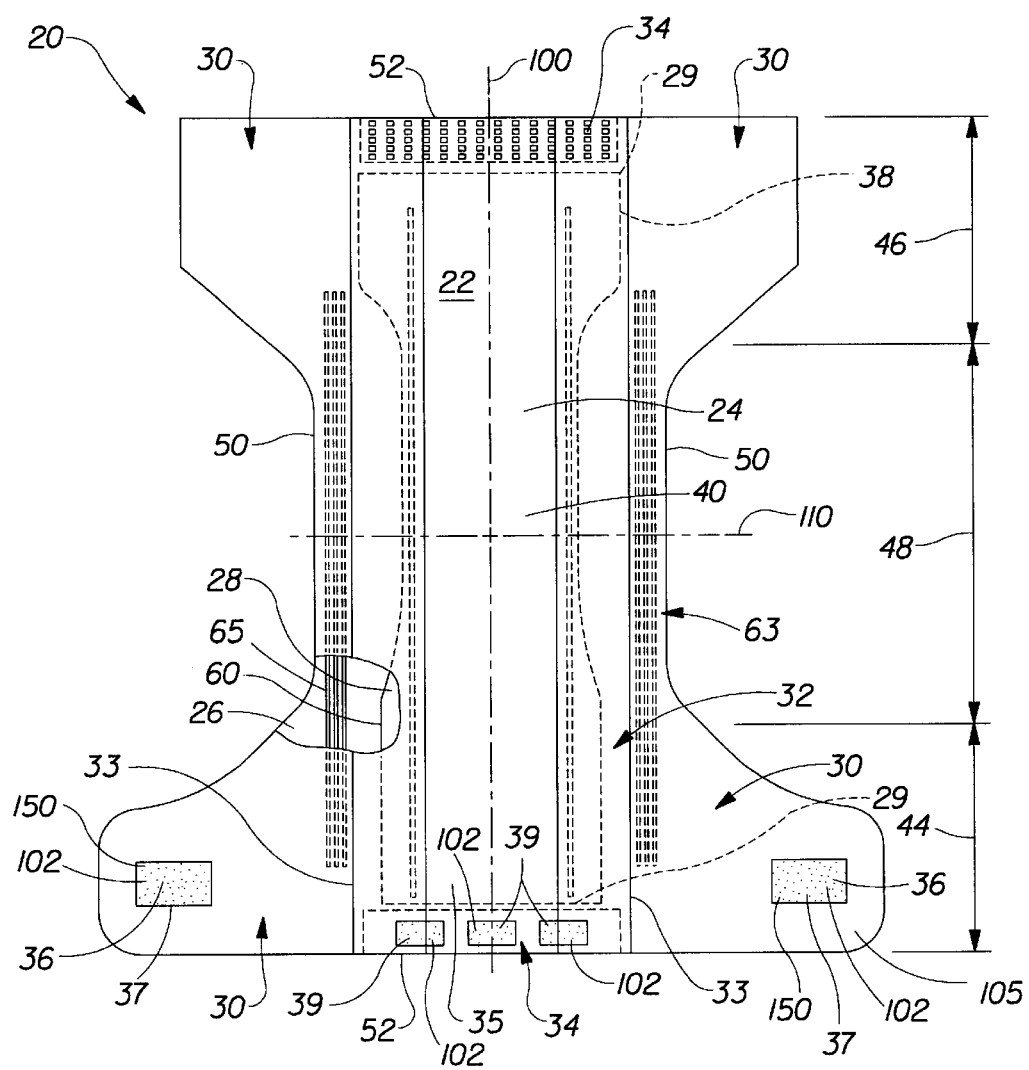
FIG. 1 is a plan view of a garment embodiment of the present invention in the form of a disposable absorbent diaper having a portion of the outer structure cut away to reveal underlying elements, showing the article in a flat condition before it has been applied to the body of a wearer.

The present invention will be described as it relates to disposable absorbent articles, in particular, to absorbent diapers and feminine protection devices, and articles to be attached to a wearer, such as body wraps. However, this invention has been contemplated for any type of a disposable garment and/or undergarment that employs polymeric materials that can be softened and drawn from the surface of the garment by application of a pressure differential. Further, the present invention can be used with non-disposable garments and/or undergarments, with woven materials such as bedsheets and tablecloths, and with other items made from flexible materials that are capable of being locally re-formed to provide the integrally-formed surface protrusions herein described.

As used herein, the term "garment" refers to an article of clothing, including undergarments such as disposable diapers, training pants, incontinence briefs, incontinence undergarments, absorbent inserts, diaper holders and liners, feminine protection devices, bandages, body wraps, bibs and the like.

As used herein, the term "garment material" refers to a single- or a multi-layered structure or a combination of a single or multi-layered structures forming at least a portion of the a chassis of the garment. Examples of garment materials may include an outer material such as a backsheet, an inner material such as a topsheet, a combination of the backsheet and topsheet, etc.

As used herein, the term "surface of the garment material" is used to mean either of the two opposing surfaces of a garment material.

As used herein, the term "absorbent article" refers to devices which absorb and contain body exudates, and more specifically, refers to devices which are placed against or in proximity to the body of the wearer to absorb and contain the various exudates discharged from the body.

The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) of the absorbent article is formed (joined and positioned) in a particular place or position as a unitary structure with other elements of the absorbent article or as a separate element joined to another element of the absorbent article.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and other incontinent persons about the lower torso.

The term "feminine protection device" refers to an absorbent article worn by women to absorb and contain menses and other vaginal exudates.

The term "body wrap" refers to an article or a garment worn about the body, typically to provide some therapeutic benefit, such as, for example, pain relief, wound coverage or to hold another device or article near the body.

Figure 2:
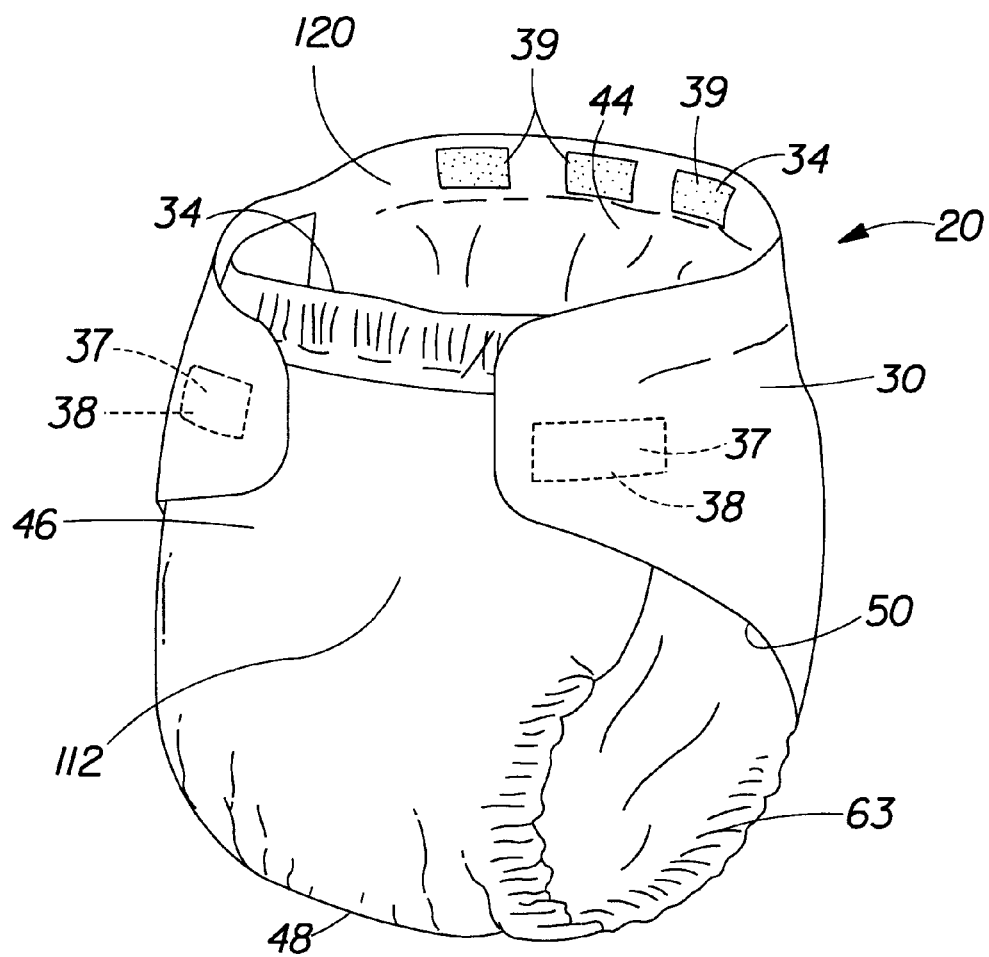
FIG. 2 is a perspective view of the disposable absorbent article of FIG. 1 in its assembled condition, as it is positioned on the body and is worn by a wearer.
Figure 21:
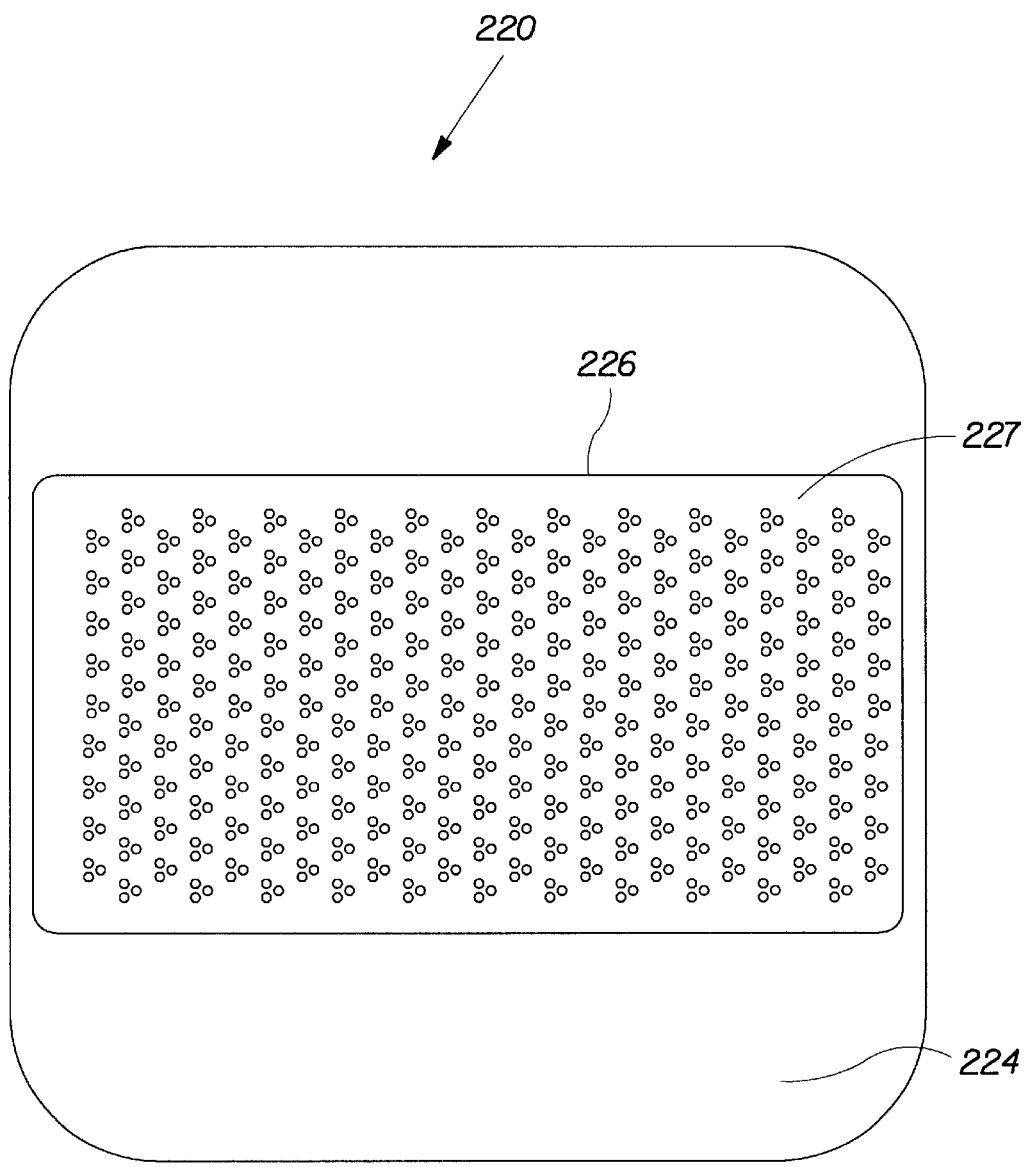
FIG. 21 is a bottom plan view of the forming die shown in FIG. 19.
Figure 25:
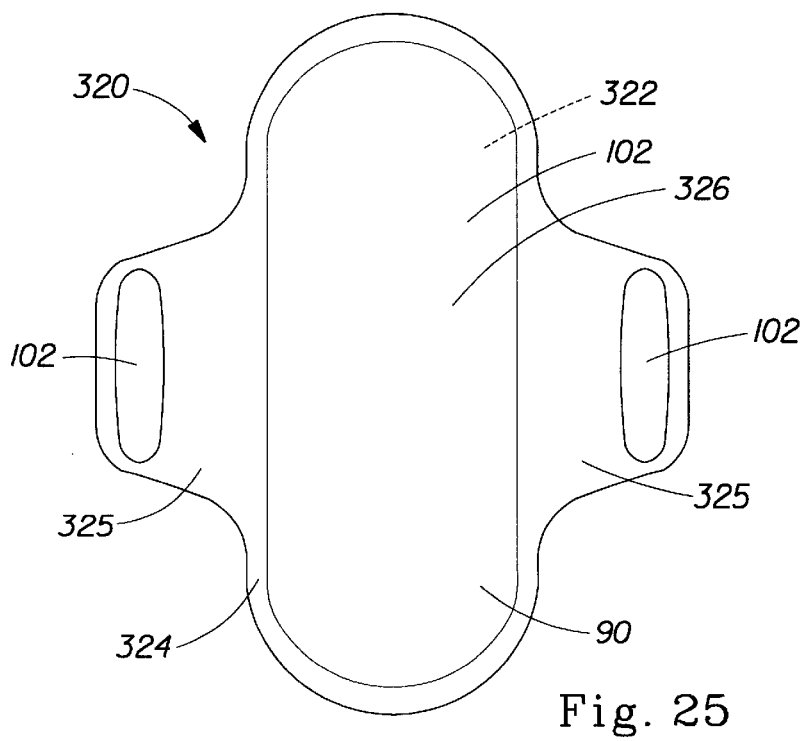
FIG. 25 is a top plan view of a sanitary napkin embodiment of the present invention.
Figure 26:
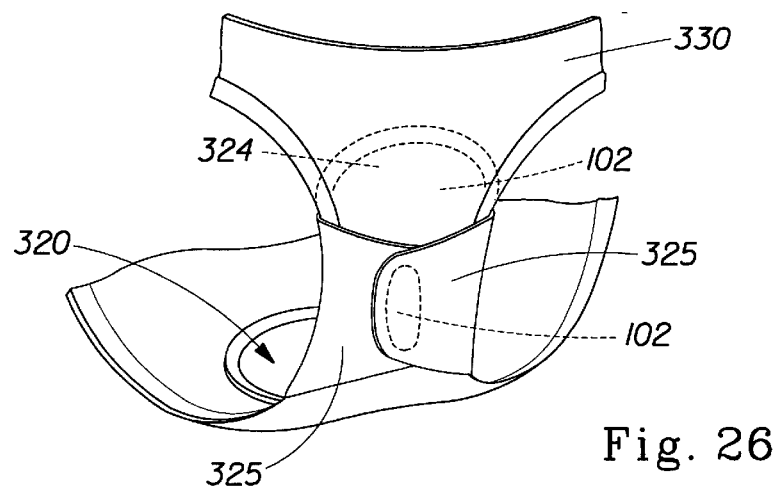
FIG. 26 is a perspective view of a sanitary napkin embodiment of the present invention as it wraps around wearer's underwear.
Figure 27:
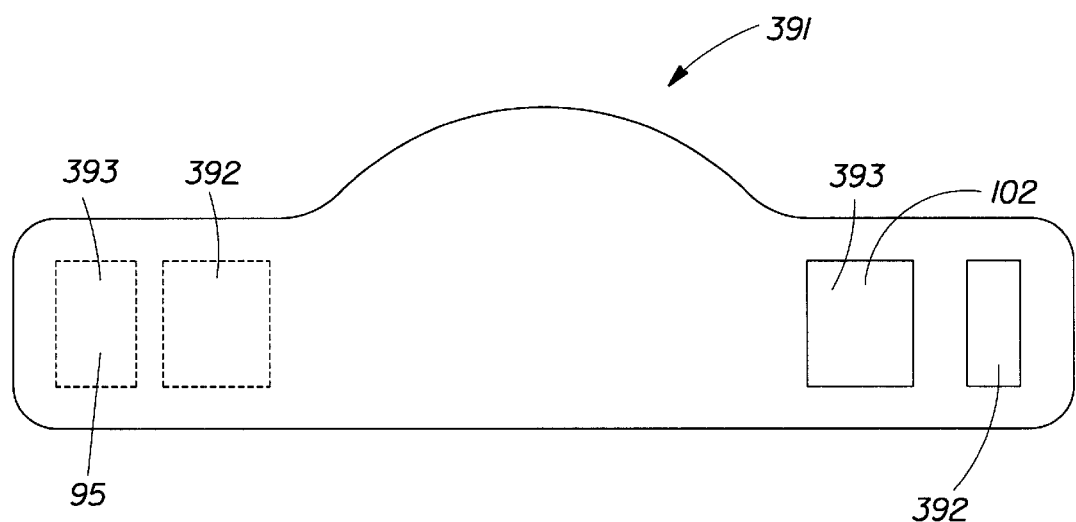
FIG. 27 is a top plan view of a body wrap embodiment of the present invention.
Figure 28:
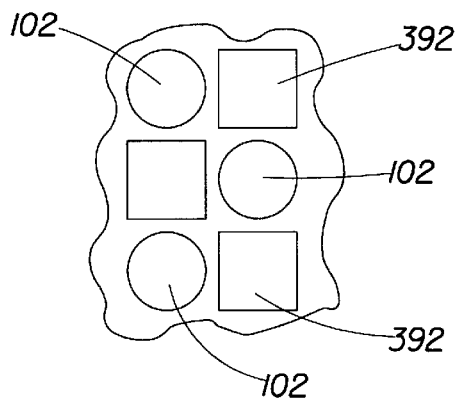
FIGS. 28–32 are top plan views of various embodiments of the surface protrusions of the present invention in combination with other fastening systems.
Figure 29:
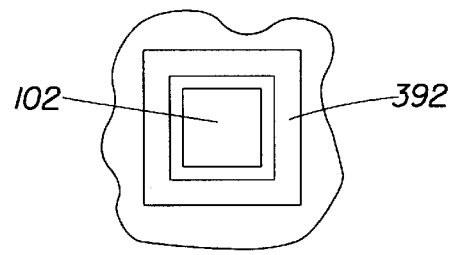
Figure 30:
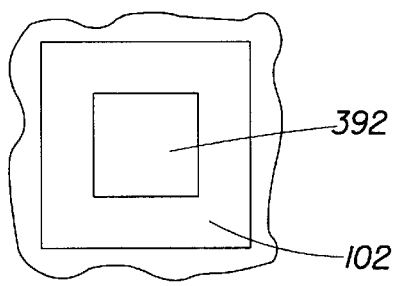
Figure 31:
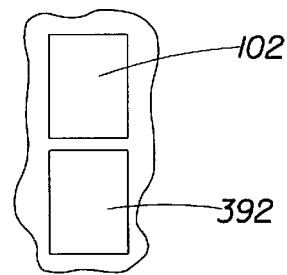
Figure 32:
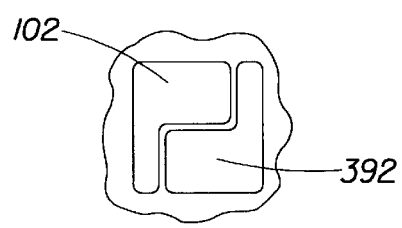

Illustrative forms of garments selected to describe the present invention are shown in FIGS. 1, 2 and 21, as a diaper 20; in FIGS. 25 and 26, as a feminine protection device 320; and in FIG. 27, as a body wrap 391. Although, as was noted above, the present invention is directed to any garment or undergarment utilizing materials which can be softened and drawn by application of a pressure differential.

FIG. 1 is a plan view of diaper 20 in a flat-out state with portions of the structure cut away to more clearly show the construction of the diaper. The portion of diaper 20 that faces the wearer is oriented toward the viewer. As shown in FIG. 1, diaper 20 preferably includes a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 36. Diaper 20 is shown in FIG. 1 to have a first waist region 46, a second waist region 44 opposed to the first waist region 46, and a crotch region 48 located between the first waist region and the second waist region. The periphery of the diaper 20 is defined by the outer edges of the diaper 20 in which the longitudinal side edges 50 run generally parallel to the longitudinal centerline 100 of the diaper 20 and the end edges 52 run between the longitudinal side edges 50 generally parallel to the lateral centerline 110 of the diaper 20.

The chassis 22 of diaper 20 forms the main body of the diaper. Chassis 22 includes at least a portion of absorbent core 28 and preferably outer covering layers including topsheet 24 and backsheet 26. Chassis 22 has an inner, body-facing surface 40, and an outer, garment-facing surface 42. If the absorbent article includes a separate holder and a liner, chassis 22 generally includes the holder and the liner. For example, the holder can include one or more layers of material to form the outer cover of the article, and the liner can include an absorbent assembly having a topsheet, a backsheet, and an absorbent core. In such cases, the holder and/or the liner can include a fastener element that is used to hold the liner in place throughout the time of use.

For unitary absorbent articles, chassis 22 includes the main structure of the diaper with other features added to form the composite diaper structure. While topsheet 24, backsheet 26, and absorbent core 28 can be assembled in a variety of well-known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; the disclosures of each of which are hereby incorporated herein by reference to the same extent as if fully rewritten.

Backsheet 26 is generally that portion of diaper 20 positioned adjacent the garment-facing surface of absorbent core 28. Backsheet 26 prevents the exudates absorbed and contained therein from soiling articles that can contact diaper 20, such as bedsheets and undergarments. In preferred embodiments, backsheet 26 is impervious to liquids (e.g., urine) and includes a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials can include breathable materials that permit vapors to escape from diaper 20 while still preventing exudates from passing through backsheet 26. Exemplary breathable materials can include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont, and in U.S. Pat. No. 5,865,823, issued to Curro on Feb. 2, 1999. Other breathable backsheets, including nonwoven webs and apertured formed films, are described in U.S. Pat. No. 5,571,096 issued to Dobrin et al. on Nov. 5, 1996. The disclosures of each of those patents are hereby incorporated herein by reference to the same extent as if fully rewritten.

Backsheet 26, or any portion thereof, can be elastically extensible in one or more directions. In one embodiment, backsheet 26 can include a structural elastic-like film ("SELF") web. SELF webs suitable for the present invention are more completely described in U.S. Pat. No. 5,518,801 entitled Web Materials Exhibiting Elastic-Like Behavior, which issued to Chappell, et, al. on May 21, 1996, the disclosure of which is incorporated herein by reference to the same extent as if fully rewritten. In alternate embodiments, backsheet 26 can include elastomeric films, foams, strands, or combinations of those or other suitable materials with nonwovens or synthetic films.

Topsheet 24 is preferably positioned adjacent the body-facing surface of absorbent core 28. The topsheet 24 is preferably compliant, soft feeling, and non-irritating to the wearer's skin. Further, at least a portion of topsheet 24 is liquid pervious, permitting liquid to readily penetrate through its thickness. A suitable topsheet 24 can be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers can be spunbonded, carded, wet-laid, meltblown, hydroentangled, or otherwise processed as is known in the art. One suitable topsheet 24 in the form of a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries" issued to Thompson on Dec. 30, 1975; U.S. Pat. No. 4,324,246 entitled "Disposable Absorbent Article Having A Stain Resistant Topsheet" issued to Mullane, et al. on Apr. 13, 1982; U.S. Pat. No. 4,342,314 entitled "Resilient Plastic Web Exhibiting Fiber-Like Properties" issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression" issued to Ahr, et al. on Jul. 31, 1984; and U.S. Pat. No. 5,006,394 "Multilayer Polymeric Film" issued to Baird on Apr. 9, 1991. Other suitable topsheets 30 may be made in accordance with U.S. Pat. Nos. 4,609,518 and 4,629,643 issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Absorbent core 28 can include any absorbent material that is generally compressible, conformable, non-irritating to the wearer's skin, and capable of absorbing and retaining liquids such as urine and other certain body exudates. Absorbent core 28 has longitudinal side edges 60 and end edges 29 and can be manufactured in a wide variety of sizes and shapes (e.g., rectangular, hourglass, "T"-shaped, asymmetric, etc.) and can include a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams, including HIPE foams; absorbent sponges; superabsorbent polymers; absorbent gelling materials; or any other known absorbent material or combinations of materials.

The configuration and construction of the absorbent core 28 may also be varied. Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735 entitled "High Density Absorbent Members Having Lower Density and Lower Basis Weight Acquisition Zones" issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From High Internal Phase Emulsions Having Very High Water-To-Oil Ratios" issued to DesMarais et al. on Jul. 22, 1997. Each of these patents is incorporated herein by reference.

Diaper 20 can also include at least one elastic waist feature 34 that helps to provide improved fit and containment. Elastic waist feature 34 is generally intended to elastically expand and contract to dynamically fit the wearer's waist. Further, diaper 20 can include side panels 30. Examples of diapers with elasticized side panels are disclosed in U.S. Pat. No. 4,857,067, entitled "Disposable Diaper Having Shirred Ears," which issued to Wood, et al. on Aug. 15, 1989; U.S. Pat. No. 4,381,781, which issued to Sciaraffa, et al. on May 3, 1983; U.S. Pat. No. 4,938,753, which issued to Van Gompel, et al. on Jul. 3, 1990; the hereinbefore-referenced U.S. Pat. No. 5,151,092, which issued to Buell on Sep. 9, 1992; U.S. Pat. No. 5,221,274, which issued to Buell on Jun. 22, 1993; U.S. Pat. No. 5,669,897, entitled "Absorbent Articles Providing Sustained Dynamic Fit," which issued to LaVon, et al. on Sep. 23, 1997; U.S. Pat. No. 6,004,306, entitled "Absorbent Article With Multi-Directional Extensible Side Panels," which issued to Robles, et al. On Dec. 21, 1999. The disclosures of each of the foregoing patents are hereby incorporated herein by reference to the same extent as if fully rewritten.

Diaper 20 may further include leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs 32 with a lotion, as described above.

Diaper 20 may also include a fastening system 36. The fastening system 36 preferably maintains the first waist region 46 and the second waist region 44 in a configuration so as to provide lateral tensions about the circumference of the diaper 20 to hold the diaper 20 on the wearer. The fastening system 36 may comprise tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. Another exemplary fastening system is disclosed in co-pending U.S. application Ser. No. 09/143,184 entitled "Absorbent Article Fastening Device" in the names of Kline et al. filed on Aug. 28, 1998. The fastening system may also provide a means for holding the garment in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 to reduce shifting of overlapped portions or to improve fit as disclosed in U.S. Pat. Nos. 5,242,436; 5,499,978; 5,507,736; 5,591,152. Each of these patents is incorporated herein by reference. In alternative embodiments, opposing sides of the garment may be seamed or welded to form a pant. This allows the garment to be used as a pull-on diaper or training pant.

Figure 23:
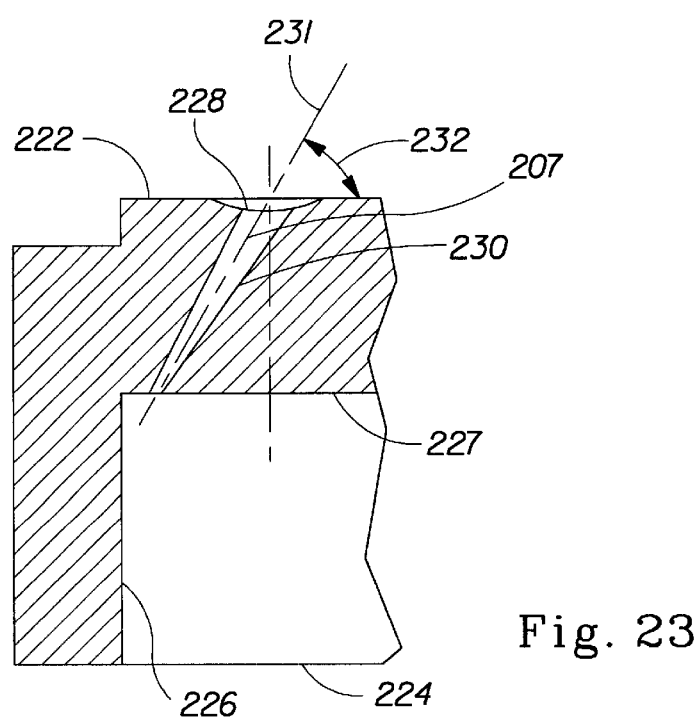
FIG. 23 is an enlarged, fragmentary cross-sectional view taken along the line 23—23 of FIG. 22.
Figure 24:
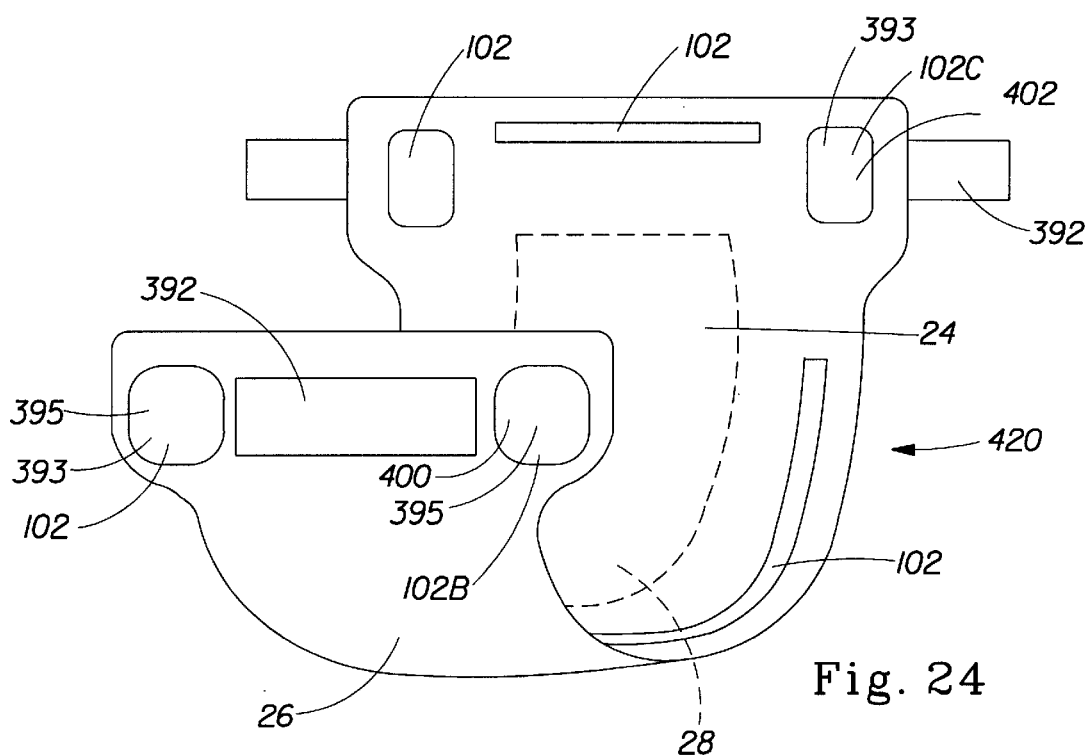
FIG. 24 is a perspective view of an alternative embodiment of a disposable diaper.

As was discussed above, other forms of garments selected to describe the present invention include sanitary napkins 320 (see FIGS. 22–23) and body wraps 391 (see FIG. 24). Typical sanitary napkins are described in U.S. Pat. No. 4,589,876 issued to Van Tilburg, May 1986; U.S. Pat. No. 4,687,478 issued to Van Tilburg Aug. 18, 1987; and U.S. Pat. No. 5,009,653 issued to Osborn on Apr. 15, 1991. Examples of interlabial feminine protection devices are disclosed in U.S. Pat. No. 5,762,644 issued to Osborn et. al. on Jun. 9, 1998. Preferred body wraps are disclosed in U.S. Pat. No. 5,860,945 issued to Cramer, et al, on Jan. 19, 1999; U.S. Pat. No. D403,778 issued to Davis, et al on Jan. 5, 1999; U.S. Pat. No. 5,741,318 issued to Oullette, et al Apr. 21, 1998. Each of these patents is incorporated herein by reference.

Diaper 20, sanitary napkin 320, and body wrap 391 may comprise surface protrusions 102 of the present invention that can be formed integrally or monolithically from at least one of the materials making up the garment material. Alternatively, surface protrusions 102 may be formed integrally from a separate material and then attached to at least a portion of the garment by any conventional means to provide any of the functions described herein. As previously descussed, the garment material can be any suitable material including a solid film, a microporous film, a nonwoven material, a woven material, a foam, a scrim or any combination thereof having a softening point of less than about 150° C.

Surface protrusions 102 can have a first cross-sectional configuration, a second cross-sectional configuration, a height, a width, a length, an angular inclination, and hook end configuration. Some non-limiting examples of various embodiments of the first cross-sectional configuration of surface configurations 102 are illustrated in FIGS. 6–12. The first cross-sectional configuration of surface protrusions 102 is a sectional view taken generally perpendicular to the surface 85 of the garment material 90 so as to divide an individual surface protrusion 102A into equal halves, and extending generally parallel to a direction defined by a projection of individual surface protrusion 102A on surface 85.

The second cross-sectional configuration of surface protrusions 102 is a sectional view taken generally parallel to the surface 85 of the garment material 90. The second cross-sectional configuration can be of any configuration, for example, a circle, an ellipse, an oval, a triangle, a square, a rectangle, an elongated rectangle and a polygonal. Further, the second cross-sectional configuration can be substantially consistent dimensionwise throughout the height H of the individual surface protrusion 102A, or it can be substantially tapered by being larger at the surface of the garment material.

The height H of surface protrusions 102 is the distance taken generally perpendicular between the surface 85 of the garment material 90 and the highest point of the individual surface protrusion 102A extending above the surface 85. In preferred embodiments, the height H of surface protrusions 102 can range from about 0.5 mm (0.02 in) to about 2.5 mm (0.10 in) or more.

The width W of surface protrusions 102 is taken at the base of the individual surface protrusion 102A in a direction defined by a projection of individual surface protrusion 102A on surface 85 of the garment material 90. In preferred embodiments, the width W of surface protrusions 102 can range from about 0.13 mm (0.005 in) to about 0.90 mm (0.035 in) or more.

The length L of surface protrusions 102 (best shown in FIGS. 13–15) is the distance at which individual surface protrusion 102A extends in a direction generally transverse to the direction of the angular inclination of the individual surface protrusion 102A. In preferred embodiments, the length L can vary from about 0.13 mm (0.005 in) to about 300 mm (12 in) or more.

Figure 6:
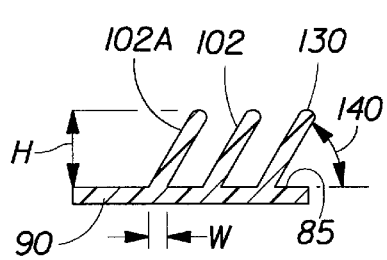
FIGS. 6 through 12 are cross-sectional views of various configurations of surface protrusions, the cross-section is taken parallel to the angle of inclination of the surface protrusions in relation to the surface of the garment material.
Figure 7:
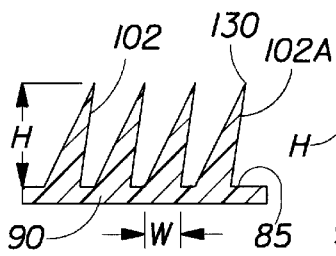
Figure 8:
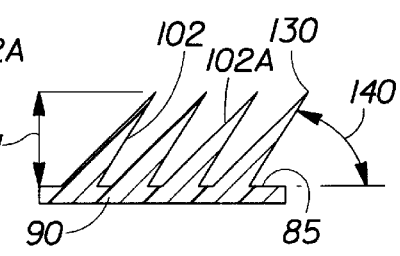
Figure 9:
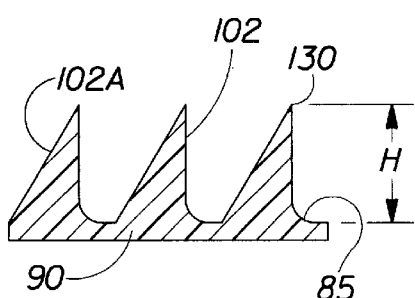
Figure 10:
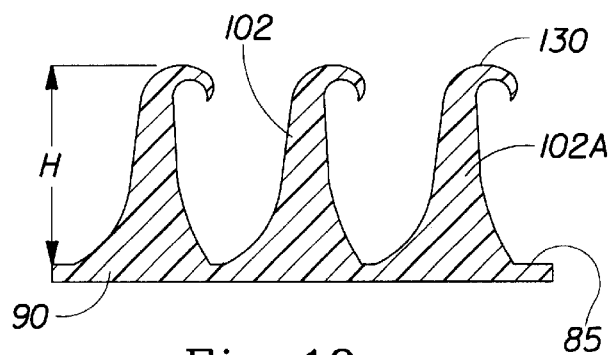
Figure 11:
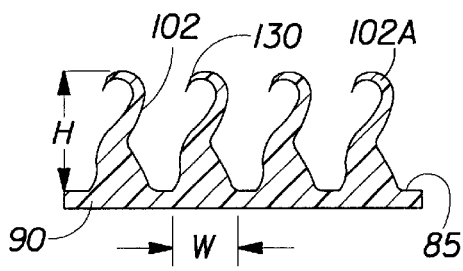
Figure 12:
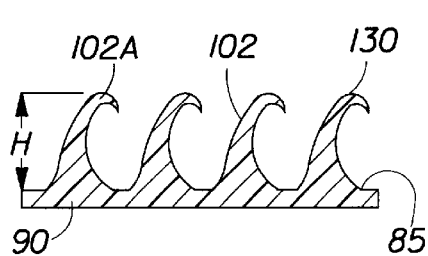

The angular inclination 140, as shown in FIG. 6, of the surface protrusions 102 relative to the surface 85 of the garment material 90 can range from an angle of about 15° to about 90°. The angular inclination of surface protrusions 102 can be uniform and/or multidirectional. Uniform angular inclination is when the directional components of individual surface protrusion 102A projected onto the surface 85 of the garment material 90 are generally parallel to each other, as shown in FIGS. 6–12. Multidirectional angular inclination is when these directional components are generally not parallel to each other, as shown, for example, in FIGS. 16–17. The hook ends 130 of the surface protrusions 102 may have various configurations as illustrated by the non-limiting examples of FIGS. 6–12.

Figure 17:
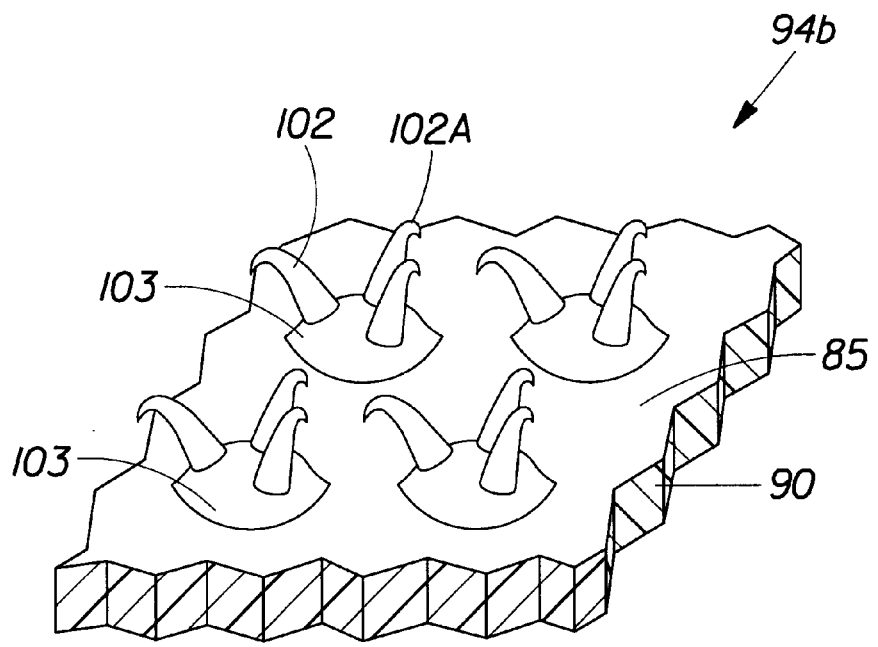
FIG. 17 is an enlarged, fragmentary, perspective view of the surface of a garment material that includes a plurality of sectors, each sector includes three outwardly-extending and multi-directionally oriented surface protrusions.
Figure 18:
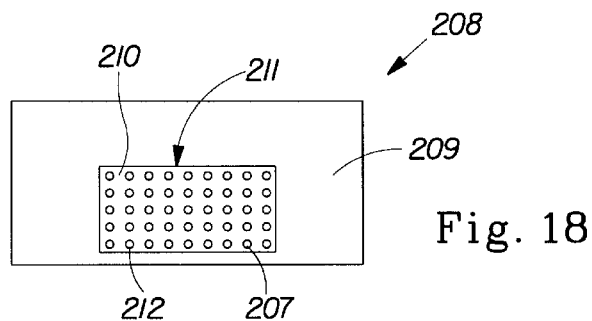
FIG. 18 is a top plan view of one embodiment of a forming die for integrally forming the surface protrusions of the present invention.
Figure 19:
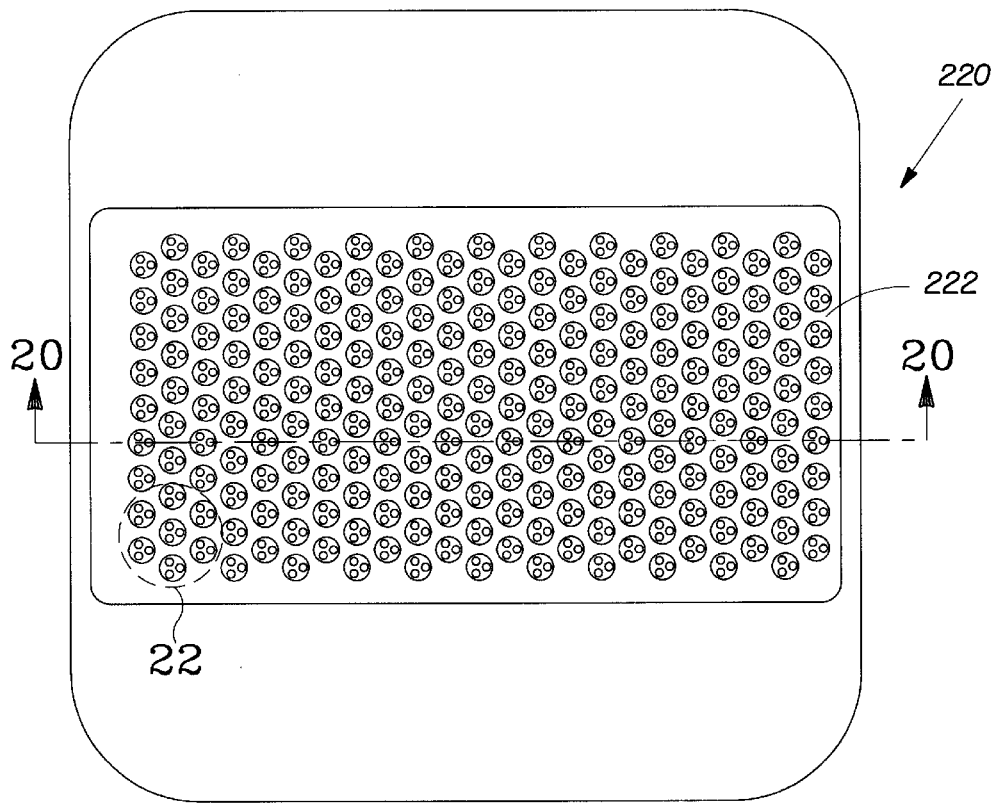
FIG. 19 is a top plan view of another embodiment of a forming die for integrally forming the sectors shown in FIG. 17.
Figure 20:
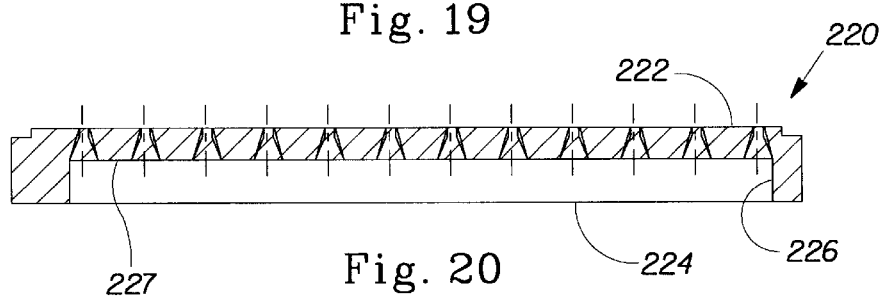
FIG. 20 is a cross-sectional view of the forming die shown in FIG. 19.

In another embodiment, surface protrusions 102 can form a plurality of sectors 94a and 94b wherein each sector may include one or more individual surface protrusions 102A extending from a base 103 as shown in FIGS. 17–18. In the 94a embodiment shown in FIG. 17, each base 103 includes two surface protrusions 102. The base 103 may also extend outwardly from the surface 85. The height, width, cross-sectional configuration, hook end configuration and angular inclination of the surface protrusions 102 in the embodiments of FIGS. 17–18 can be similar in all or any aspects to the height, cross-sectional configuration, hook end configuration and angular inclination of the surface protrusions 102 in the embodiments of FIGS. 6–12.

In the embodiment shown in FIG. 17, each inclined surface protrusion 102A has a directional component projected onto the surface 85 of the garment material 90 that extends from the base 103 in a direction that is substantially 180° from the direction in which the projection of the opposed, second surface protrusion extends. Although shown as substantially 180° apart, surface protrusions 102 can also be oriented so that their respective angular separation is less than 180°. When so oriented, the angular separation of surface protrusions 102 can be from about 30° to about 180°, more preferably from about 90° to about 180°.

In the embodiment shown in FIG. 17, each of the bases 103 includes three individual surface protrusions 102A that extend in different directions. Preferably each of the inclined surface protrusions has a directional component projected onto surface 85 of garment material 90 that extends from base 103 in a direction that is substantially 120° from the direction in which the projection of the adjacent surface protrusion extends. Although shown as substantially 120° apart, surface protrusions 102 can also be so oriented that their angular spacing is different from 120°, if desired.

Figure 13:
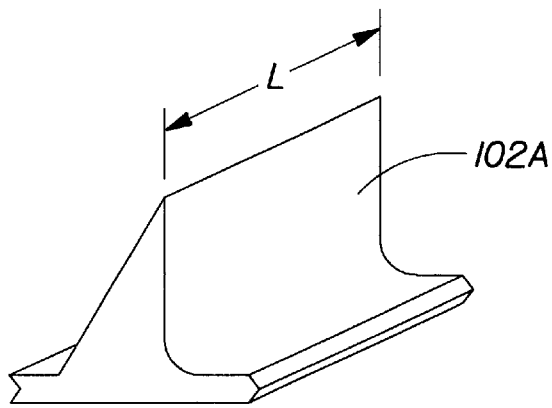
FIG. 13 is a perspective view of an individual surface protrusion shown in FIG. 9.
Figure 14:
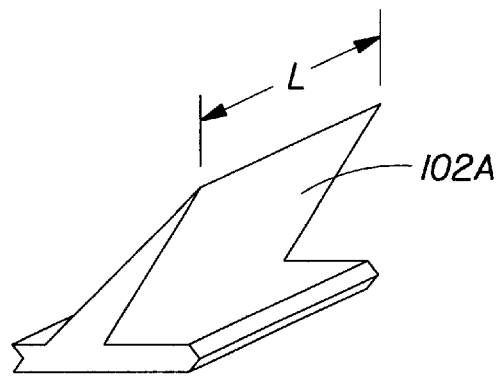
FIG. 14 is a perspective view of an individual surface protrusion shown in FIG. 8.
Figure 15:
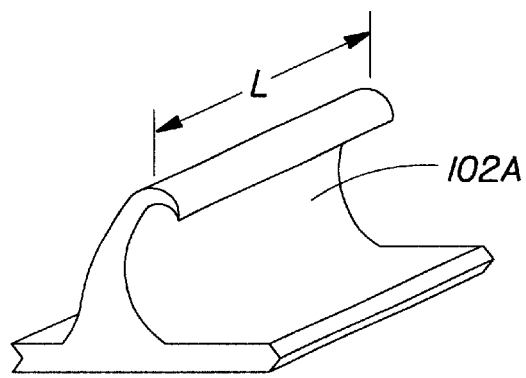
FIG. 15 is a perspective view of an individual surface protrusion shown in FIG. 12.

Garment material 90 can be mechanically modified to form surface protrusions 102 integrally from the garment material 90, for example, by placing surface 85 of garment material 90 against a forming die 208, as shown in FIG. 18. As used herein, the term "mechanically modified" refers to processes that involve a physical change to a material as opposed to a chemical change, such as, for example, softening a material, melting a material, drawing a material under applied pressure differential, cooling a material, etc. The forming die 208 may have a plurality of openings 207 in form of substantially rounded bores and/or elongated slots. For example, the forming die 208, as shown in FIG. 18, has a plurality of openings 207 in form of bores 212 in a die face 210. Bores 212, for example, can have a length of about 2.54 mm (0.1 in.), a diameter of about 0.63 mm (0.025 in.), and a center-to-center spacing of about 1.27 mm (0.050 in.). The dimensions of bores 212, however, can be changed to suit particular requirements of the surface protrusions. The slots also can be of any length suitable to provide any desirable length L of individual surface protrusions 102A, as shown in FIGS. 13–15 and described above. The bores and/or slots can have their axes 231 (best shown in FIG. 23) disposed at an angle 232 (best shown in FIG. 23) ranging from about 15° to about 90° relative to the surface of the die.

The die face 210 of the die 208 can be of any size to suit a required surface protrusion area 211, as shown in FIG. 18. The surface protrusion area 211 can be of any size to suit specific design requirements of the garment having surface protrusions. The surface protrusion area 211 shown in FIG. 18 is, for example, about 24.13 mm (0.950 in.) long and about 11.43 mm (0.450 in.) wide. As will be appreciated, those dimensions, as well as the geometrical form of the array of surface protrusions, can be changed to suit particular requirements of the surface protrusions.

Openings 207 have innermost ends that are preferably rounded and that include a narrow passageway that extends from the interior of the opening 207 to a die rear surface 227 (best shown in FIG. 23) to provide communication between the die face and the rear surface of the die to create a pressure differential inside the respective openings so that softened garment material can be drawn into the openings to form the surface protrusions 102. The openings 207 generally have a configuration and orientation corresponding with the desired shape and orientation of the surface protrusions 102. The openings 207 can be formed in the die by electrical discharge machining, by laser machining, by photo etching, by drilling, milling or the like.

In use, the forming die 208 is placed against the garment surface 85 of the garment material 90 onto which the surface protrusions 102 are desired to be integrally or monolithically formed and a pressure differential is created between the opposite ends of the openings 207. Thus, a lower pressure is created at the ends of the openings which are spaced from the garment surface 85. It should be noted that the pressure differential can be created by any conventional means. However, in preferred embodiments of the present invention, the pressure differential may be created by applying a vacuum to the ends of the openings which are spaced from the garment surface. The vacuum level can range from about 0.1 inch of water to about 25 inch of water The garment material 90 is then softened by heating the garment material 90, either by applying external heat or by generating heat internally within the garment material by applying ultrasonic vibrations, microwaves, radio waves, infrared waves, a laser beam, an electron beam, induction heating, or the like. In any event, the garment material 90 is softened and a portion of the softened garment material is drawn into the openings 207 by the reduced pressure within the openings 207 resulting from the vacuum imposed on the outer ends of the openings 207. The amount of garment material 90 drawn and the shape of the surface protrusions 102 can be varied as needed by changing the level of pressure differential created between the openings 207. After the softened garment material 90 has been drawn into the openings 207, the source of heat is withdrawn to allow the garment material 90 to at least partially cool. The forming die 208 is then separated from the garment surface 85, whereupon the garment material 90 and the resulting surface protrusions cool to provide the desired surface protrusions 102. It should be noted that the garment material does not adhere to any portion of the forming die and, after formation of the surface protrusions, the surface protrusions are readily released from the forming die.

Figure 16:
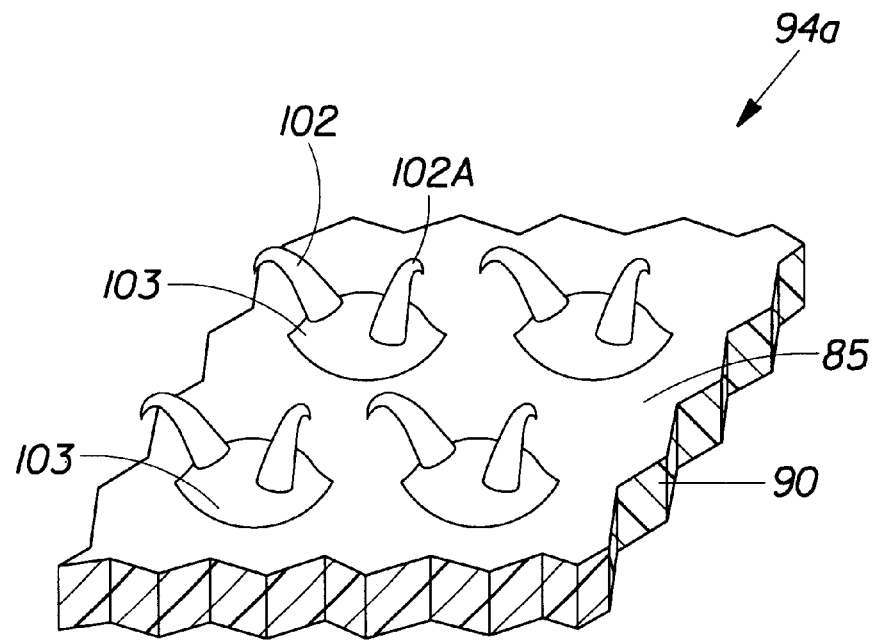
FIG. 16 is an enlarged, fragmentary, perspective view of the surface of a garment material that includes a plurality of sectors, each sector includes two outwardly-extending surface protrusions.
Figure 22:
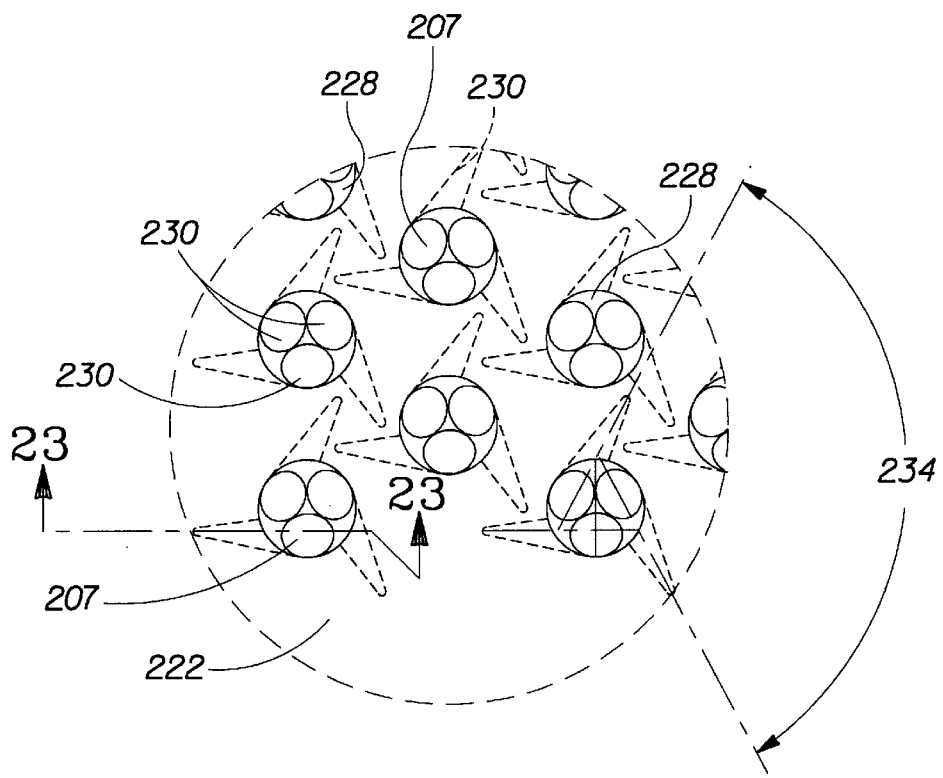
FIG. 22 is an enlarged, fragmentary view of a portion of the top surface of the forming die shown in FIG. 19.

Another configuration of a forming die, one that can be employed to form surface protrusions 102 illustrated in FIGS. 16–17, is shown in FIGS. 19–23. Forming die 220 includes an upper surface 222 and a lower surface 224 in which a recess 226 is formed to define an inner die surface 227. A series of spaced, preferably shallow recesses 228 that can be of spherical curvature, as best shown in FIGS. 22–23, are formed in upper surface 222 of forming die 220, and three equally-angularly-spaced openings 230 are provided to extend from the surfaces of recesses 228 to the surface of recess 226 on lower surface 224 of forming die 220. It should be noted, however, that the recess 228 can have any suitable shape to provide a suitable recess to form the base 103 of the surface protrusions 102.

Referring to FIGS. 22–23, the axes 231 of openings 230 are inclined relative to upper surface 222 of the forming die 220 at an angle 232 of about 60°, and they are disposed relative to each other at an angle 234 of about 120°. Each of openings 230 is of tapered form, having a greater area at recess 228 than at inner die surface 227. The inner die surface 227 has preferably relatively small openings ranging from about 0.1 mm (0.004 inch) to about 1.5 mm (0.060 inch) to permit communication between the openings 230 and the source of vacuum to enable the softened substrate material to be drawn into openings 230 and recess 228 to form the surface protrusions 102.

The mechanical formation of surface protrusions described herein can be carried out by a forming die, either stationary or in motion. For example, although shown and described herein as a flat surface forming die, it will be apparent that the forming die can also be provided with a curved outer surface, to enable it to be carried on a rotary carrier so that the surface protrusion formation process can be affected by a rotating forming die for forming the surface protrusions at a higher speed than would be possible by utilizing only an oscillating, back-and-forth movement between a forming die and a backing member.

Regardless of the specific embodiment, it should be noted that configuration of the surface protrusions can depend upon several factors. For example, the ratio of the surface protrusion height to the surface protrusion width, the depth of the openings of the forming die, the level of softening of the garment material, the level of applied vacuum to draw the softened garment material and the parameters of the cooling conditions can all affect the final form of the surface protrusions.

The surface protrusions 102 can be located in surface protrusion areas 150, as shown in FIG. 1, which can include any number of surface protrusions. The term "surface protrusion area" refers herein to a local area of a garment which encircles an array of surface protrusions distributed throughout that area. The surface protrusion area can be of any size, shape and density. The surface protrusion areas 150 of the present invention can have various sizes and shapes, including aesthetically pleasing shapes, non-limiting examples of which are shown in FIGS. 3A through 3M. The surface protrusion areas 150 may form any pattern, including stripes, circles, squares, polygons, series of dots or other regular shapes, or irregular swirls or stripes such as random or irregular patterns including but not limited to spirals or random patterns. Further, the surface protrusion areas 150 can have various densities. By the "density" is meant herein the number of surface protrusions per an area unit (inch or mm) of the surface protrusion area. The density of the surface protrusion area normally affects flexibility and softness of hook-and-loop type fasteners. For example, a lower density area generally provides higher material flexibility and softness. However, in order to provide a certain holding force between the engaging hooks and loops, a certain number of hooks must be available for engagement. Therefore, it may be desirable to distribute the hooks among a larger area of a material than the area provided by conventional tapes carrying hook fasteners. Enlarging the area provided by conventional hook-and-loop type fasteners though may increase the cost of these fasteners. Thus, it may be advantageous to employ the surface protrusions of the present invention, as all or a portion of the fastener system, to reduce the cost and increase flexibility and softness of the garment.

In certain embodiments of diaper 20, as shown in FIG. 1, at least a portion of the fastening system 36 may comprise surface protrusions 102. For example, the surface protrusions 102 may serve as a primary fastening system or a component thereof; a secondary fastening system or a component thereof; or as a supplemental fastener. It should be noted, however, that surface protrusions 102 may be used on any of the above fastening systems 36 individually or in combination. A primary fastening system generally provides a primary connection between a first portion and a second portion of a garment to hold the garment about the wearer. Examples of primary fastening systems are disclosed in more details in previously referenced U.S. Pat. Nos. 4,699,622, and 4,894,060. Also, the primary fastening system may be used to help maintain the absorbent article in a closed, wrapped configuration for disposal to provide more convenient disposal of the used article.

A secondary fastening system generally provides resistance to shifting of any overlapped portions or components of a garment to improve fit. Examples of secondary fastening systems are disclosed in more details in previously referenced U.S. Pat. No. 4,699,622.

A supplemental fastener generally provides increased resistance to disengagement of the primary fastening system and/or secondary fastening system. For example, the supplementary fastening system can improve resistance to disengagement in a peel mode and/or a shear mode of disengagement to supplement the fastening strength of the primary and/or secondary fastening system as described herein. A peel mode of disengagement of two portions of a garment connected at their respective surfaces may exist, for example, when the two portions of the garment are pulled apart by oppositely directed forces each having a force component which is generally perpendicular to the connected surfaces. A shear mode of disengagement, in comparison, exists when the two portions of a garment components are pulled apart by oppositely directed forces each having a force component which is generally parallel to the connected surfaces.

Surface protrusions 102 may provide primary fastening functions on garments, such as, for example, a diaper, a body wrap, and a sanitary napkin. FIG. 24 shows diaper 420 having a primary fastening system 392 which may comprise surface protrusions 102. FIG. 27 shows an example of a body wrap 391 having a primary fastening system 392 which may also comprise surface protrusions 102. FIGS. 25–26 show an example of a sanitary napkin 320 having surface protrusions 102 providing the primary fastening function. In sanitary napkin embodiments, the surface protrusions 102 may be disposed in a backsheet 324, flaps 325 or both. In the embodiment 320 shown in FIGS. 22–23, surface protrusions 102 join flaps 325 of sanitary napkin 320 to the wearer's underwear or to each other. However, it should be noted that the sanitary napkin need not have flaps to function in accordance with the present invention. For example, surface protrusions 102 may connect a body 326 of sanitary napkin 320 directly to the wearer's underwear 330.

In embodiments where the primary fastening systems function to maintain the absorbent article in a wrapped configuration for disposal, surface protrusions 102 may be disposed on the body facing surface of the garment (e.g., diaper 20 shown in FIG. 24). In other embodiments, the surface protrusions 102 may also or alternatively be disposed on the outer surface of the garment in a position to maintain the garment in a disposal configuration. Further, the surface protrusions 102 may be disposed on a fastening tape attached to the garment in place of an adhesive portion. Examples of such adhesive attachments are disclosed in U.S. Pat. No. 5,019,065. The surface protrusions 102 may be used with many other tape designs to secure the garment for disposal, including disposal tape systems disclosed in U.S. Pat. Nos. 5,108,384; 4,869,724; 5,575,784; 5,626,573; and 5,279,604 and publications WO 98/53780 and WO 99/17693. Each of the above patents and publications is incorporated by reference herein.

As described above, the surface protrusions 102 may also provide a secondary fastening function. For example, FIG. 24 shows diaper 20 having a secondary fastening system 393 which may comprise surface protrusions 102 to prevent shifting of overlapped portions of diaper 20 during use. In another example, shown in FIG. 27, a body wrap 391 has a secondary fastening system 393 which comprises surface protrusions 102 and a primary fastening system 392 which may comprise, for example, hook and loop fasteners for securing one portion of the body wrap 391 to itself to provide primary securement of the body wrap 391 to the wearer. In any case, the secondary fastening system may comprise other elements, such as, for example, pressure sensitive adhesives, mechanical fasteners, etc.

The surface protrusions 102 may also provide a supplemental fastening function. When used as a supplemental fastener, surface protrusions 102 may be used in conjunction with any type of primary fastening system 392 as described herein and shown in one example in FIG. 27 to supplement the primary fastening system's 392 fastening strength, thereby increasing the resistance to removal versus the use of the primary fastener alone. Preferably, in these embodiments, the surface protrusions 102 may increase the peel and/or shear strength of the fastener by at least about 10%, or may increase the peel and/or shear strength by at least about 25%, about 50%, about 100% or more.

In providing supplemental fastening functions, surface protrusions 102 may be part of or separate from the primary fastening system. For example, surface protrusions 102 may be placed laterally inward or laterally outboard of the primary fastening system 392, longitudinally above or below the primary system 392, or even be coincident or interleaved with the primary fastening system 392.

Some exemplary approaches to placing the protrusions 102 coincident with the primary fastening system 392 are disclosed in publications WO 95/25905 and WO 98/10728, each of which is incorporated herein by reference. Further, surface protrusions 102 may replace the cohesive portion of the 2-mechanism mechanical-cohesive system described in WO 95/25905 on either the hook portion, the loop portion, or both portions of the 2-mechanism system, and which is incorporated by reference herein. Alternatively, surface protrusions 102 may replace the bonding element at the base of the loops described in WO 98/10728, which is incorporated by reference herein. Yet other embodiments of coincident systems provide one or more regions of surface protrusions 102 among one or more other fasteners, examples of which are shown in FIGS. 28–32.

In further preferred embodiments of supplemental fastening systems, surface protrusions 102 may be used in conjunction with a tab and slot fastening system (such as disclosed in previously referenced co-pending U.S. application Ser. No. 09/143,184) to supplement the strength of the tab and slot fastening system. In such embodiments, the surface protrusions 102 may be disposed on the tab member, the slot member, or both and may engage into complementary surface protrusions to increase the fastening strength of the tab and slot system.

Surface protrusions 102 may be engaged with protrusion receiving zones to connect one portion of the garment to another portion of the garment. The garment may include at least one protrusion receiving zone 395, as shown in one example in FIG. 24. The protrusion receiving zone 395 provides a location at which surface protrusions 102 connect at least one portion of the garment to at least one another portion of the garment. The relative positions of surface protrusions 102 and protrusion receiving zone 395 can vary. For example, surface protrusions 102 may be disposed on the body facing surface of the garment and protrusion receiving zone 395 may be disposed on the outer surface of the garment. Alternatively, protrusion receiving zone 395 may be disposed on the body facing surface of the garment and/or surface protrusions 102 may be disposed on the outer surface of the garment. Further, protrusion receiving zone 395 and surface protrusions 102 may both be disposed on the body facing surface of the garment and/or both be disposed on the outer surface of the garment. In any case, protrusion receiving zone 395 may be a separate piece of material added to the diaper or may be an integral or monolithical part of the diaper, including but not limited to the topsheet, the backsheet, the leg cuff, or the waistband.

Figure 4:
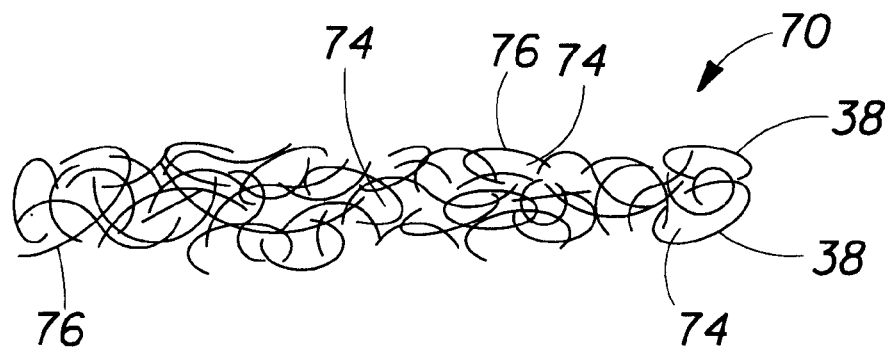
FIG. 4 is an enlarged, fragmentary, cross-sectional view of a garment material which includes a nonwoven fibrous material.
Figure 5:
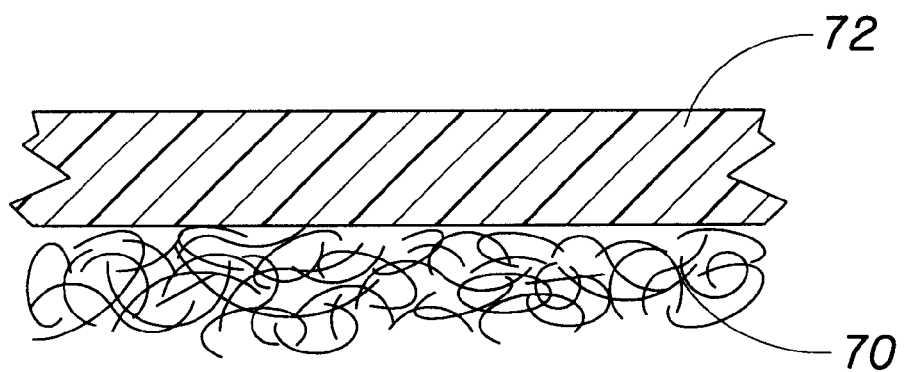
FIG. 5 is an enlarged, fragmentary, cross-sectional view, similar to that of FIG. 4, showing a garment material which includes a nonwoven fibrous material joined in face-to-face relationship with a film material.

Protrusion receiving zone 395, as shown in FIG. 24, may comprise any suitable loop or landing material which engages with the surface protrusions 102 of the present invention. In one preferred embodiment, protrusion receiving zone 395 may comprise fiber loops or at least one nonwoven layer of material. For example, referring to FIG. 4, there is shown an enlarged cross section of a nonwoven substrate 70 that can be applied in overlying relationship to the outwardly-facing surface of a. polymeric layer 72 (see FIG. 5) to provide a plurality of loops in the form of preferably closed loops 38. Loops 38 define spaced open areas bounded by interengaged individual fibers 76. FIG. 6 shows an alternative embodiment of a garment material having nonwoven substrate 70 attached to both the outwardly-facing and the inwardly-facing surfaces of the polymeric layer 72. In yet another embodiment, as shown in FIG. 24, protrusion receiving zone 395 may comprise a first area 400 of surface protrusions 102B which engages with a second area 402 of surface protrusions 102C. In such embodiments, engaging first area 400 of surface protrusions 102B in protrusion receiving zone 395 with second area 402 of surface protrusions 102C may provide minimal resistance to peel mode disengagement and may provide an increase in friction or shear mode disengagement resistance between the portions of the garment being engaged. For example, as shown in FIG. 24, at least a portion of the backsheet 26 may serve as a protrusion receiving zone 395 and may comprise surface protrusions 102, thus allowing the backsheet 26 to serve as a portion of the fastening system 36. Surface protrusions 102 of protrusion receiving zone 395 may engage with surface protrusions 102 of secondary fastening system 393. If surface protrusions 102 are formed integrally from the backsheet 26, surface protrusions 102 of receiving zone 395 may form at least a portion of an integral backsheet landing zone. Other integral backsheet landing zones which may be used in conjunction with surface protrusions 102 are disclosed in U.S. Pat. Nos. 5,846,365 and 5,735,840 issued to Kline, et al on Dec. 8, 1998 and Apr. 4, 1998, each of which in incorporated herein by reference.

In an alternative embodiment of the present invention, the surface protrusions 102 may provide a higher effective coefficient of friction between the garment and the wearer's skin, thus providing at least some additional resistance to the garment slipping downward or moving in other undesirable ways during use. In these embodiments, the surface protrusions 102 may be located on any body-contacting surface of the garment. In certain preferred embodiments, as shown in FIGS. 1 and 24, the surface protrusions may be located in proximity to the perimeter of the garment, such as the side margins, leg cuffs, or waist region, especially in the laterally outboard portions of the waist regions, and most preferably in the laterally outboard portions of the rear waist region. Particularly preferred locations for the surface protrusions for this use are disclosed as the locations for the garment retention zones in co-pending U.S. patent application Ser. No. 09/312,997 entitled "Disposable Absorbent Article Having Article Retention Zones" filed May 17, 1999 in the names of Ashton et al. The above identified patent application is hereby incorporated by reference herein. In alternative embodiments of the present invention, the surface protrusions 102 may be disposed on a topsheet in the crotch region. This may be especially useful for feminine protective devices embodiments where the article is a pad which may not have another fastening system to hold the pad on the wearer.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A garment having a first region and a second region opposed to the first region, the garment comprising:

a garment material extending through at least a portion of the first region, the garment material having a surface wherein at least a portion of the surface has been mechanically modified to form a plurality of surface protrusions integrally from the garment material and not separately joined to the garment material; and a landing zone having a plurality of fibrous loops located at least partially in the second region and adapted to engage with the surface protrusions of the first region to provide a closure mechanism for holding the first region and the second region in an overlapping configuration.

2. The garment of claim 1 wherein the garment material is selected from a group consisting of a solid polymeric material, an apertured polymeric material, a fibrous non-woven material and fibrous woven material.

3. The garment of claim 1 wherein the garment material is defined by a laminate structure which includes at least one liquid pervious layer.

4. The garment of claim 1 wherein the garment material is defined by a laminate structure which includes at least one liquid impervious layer.

5. The garment of claim 1 wherein the surface protrusions have a cross-sectional configuration which is selected from a group consisting of a circle, an ellipse, an oval, a triangle, a square, a rectangle, an elongated rectangle and a polygonal.

6. The garment of claim 1 wherein the surface of the garment material forms an inner surface of the garment facing the body of a wearer.

7. The garment of claim 1 wherein the surface of the garment material forms an outer surface of the garment opposing the body of a wearer.

8. The garment of claim 1 wherein the surface protrusions are adapted to be releasably engaged with the fibrous loops.

9. The garment of claim 1 wherein the surface of the garment material further includes at least one base formed integrally from the garment material and extending outwardly from the surface of the garment material, the base having at least two surface protrusions extending outwardly from the base.

10. The garment of claim 1 wherein the garment is selected from a group consisting of: a disposable absorbent article, a disposable diaper, a feminine protection device and a body wrap.

11. The garment of claim 10 further comprising at least one side panel, at least a portion of the side panel including the surface protrusions.

12. The garment of claim 10 further comprising at least one wing, at least a portion of the wing including surface protrusions.

13. A garment having a first region and a second region opposed to the first region, the garment comprising:
- a garment material capable of being softened and drawn under a vacuum, the garment material extending at least partially in the first region, the garment material having a surface wherein at least a portion of the surface has been mechanically modified to form a plurality of surface protrusions integrally from the garment material, the surface protrusions having a configuration and an orientation in relation to the garment surface, the surface protrusions being formed from the garment surface by the steps of:
  i) providing a portion of the garment including the garment surface onto which the surface protrusions will be formed;
  ii) providing a forming die having a first surface and a second surface opposed to the first surface, the first surface having a plurality of openings which have a configuration and orientation corresponding with the shape and orientation of the surface protrusions of the garment material, the openings providing communication between the first surface and the second surface of the forming die;
  iii) placing the garment surface against the first surface of the forming die;
  iv) softening the garment surface by application of a source of energy;
  v) applying a vacuum to the second surface of the forming die to draw at least some of the softened garment surface into the openings from the first surface of the forming die; and
  vi) separating the forming die from the garment surface to form the surface protrusions; and
- a landing zone having a plurality of fibrous loops located at least partially in the second region and adapted to engage with the surface protrusions of the first region to provide a closure mechanism for holding the first region and the second region in an overlapping configuration.

14. The garment of claim 13 wherein the garment material is softened by application of the energy source selected from a group consisting of: induction heating, ultrasonic vibrations, micro waves, radio waves, infrared waves, a laser beam and an electron beam.

15. The garment of claim 13 wherein the surface protrusions have a second cross-sectional configuration which is selected from a group consisting of a circle, an ellipse, an oval, a triangle, a square, a rectangle, an elongated rectangle and a polygonal.

16. The garment of claim 13 wherein the garment is selected from a group consisting of: an absorbent article, a diaper, a feminine protective device and a body wrap.

17. The garment of claim 16 wherein the garment is a disposable article.

18. The garment of claim 13 further comprising an inner surface adapted to contact the skin of a wearer, at least a portion of the inner surface includes the surface protrusions.

19. The garment of claim 13 further comprising a receiving zone adapted to releasably engage with the surface protrusions when the garment is configured about the wearer.

20. The garment of claim 13 wherein the surface protrusions are integrally formed from the garment surface.

21. The garment of claim 13 wherein the surface protrusions are integrally formed from a material which is separately added to the garment surface.

22. The garment of claim 13 further comprising a fastening system having the surface protrusions.

23. The garment of claim 22 wherein the fastening system is selected from a group consisting of a primary fastening system, a secondary fastening system and a disposal fastening system.

* * * * *